(12) United States Patent (10) Patent No.: US 9,358,052 B2
Hansson (45) Date of Patent: Jun. 7, 2016

(54) METHOD FOR FIXATION OF BONE FRAGMENTS AT BONE FRACTURES

(71) Applicant: Henrik Hansson, Vreta Kloster (SE)

(72) Inventor: Henrik Hansson, Vreta Kloster (SE)

(*) Notice: Subject to any disclaimer, the term of this patent is extended or adjusted under 35 U.S.C. 154(b) by 0 days.

(21) Appl. No.: 14/715,825

(22) Filed: May 19, 2015

(65) Prior Publication Data

US 2015/0250511 A1 Sep. 10, 2015

Related U.S. Application Data

(63) Continuation of application No. 12/670,156, filed as application No. PCT/SE2008/050848 on Jul. 8, 2008.

(30) Foreign Application Priority Data

Jul. 24, 2007 (SE) ...................................... 0701776

(51) Int. Cl.
*A61B 17/76* (2006.01)
*A61B 17/80* (2006.01)
*A61B 17/17* (2006.01)
*A61B 17/74* (2006.01)
*A61B 17/84* (2006.01)
(Continued)

(52) U.S. Cl.
CPC .......... *A61B 17/8057* (2013.01); *A61B 17/1721* (2013.01); *A61B 17/1728* (2013.01); *A61B 17/1742* (2013.01); *A61B 17/746* (2013.01); *A61B 17/846* (2013.01); *A61B 17/86* (2013.01); *A61B 2017/681* (2013.01)

(58) Field of Classification Search
CPC ........... A61B 17/1721; A61B 17/1728; A61B 17/746; A61B 17/8057; A61B 17/8052
See application file for complete search history.

(56) References Cited

U.S. PATENT DOCUMENTS 2,627,855 A 2/1953 Price
4,959,064 A * 9/1990 Engelhardt ...................... 606/65
4,964,403 A 10/1990 Karas et al.
(Continued)

FOREIGN PATENT DOCUMENTS

EP 0617927 10/1994
JP 2007090094 4/2007
(Continued)

OTHER PUBLICATIONS

Instruction Manual Type Gunclean Toftejorg SSt40T, Jun. 9, 2012.

*Primary Examiner* — Mary Hoffman
(74) *Attorney, Agent, or Firm* — Tarolli, Sundheim, Covell & Tummino LLP

(57) ABSTRACT

The present invention relates to a device for fixation of bone fragments at bone fractures. The device comprises at least two fixation means (5, 6) and a securing plate (4). With the object of preventing or counteracting re-dislocation, the respective fixation means (5, 6) each have a first fixing portion (19) for fixing the fixation gleans in an inner bone fragment (3), a second fixing portion (21) for locking the fixation means to the securing plate (4) which is disposed on the outside of an outer bone fragment (2) and allows movement of the outer bone fragment relative to it, so that the fixation means are prevented from changing their angular position relative to the securing plate and relative to one another, and a middle portion (22) which is situated between the fixing portions and runs through the outer bone fragment, along which middle portion the outer bone fragment can slide inwards towards the inner bone fragment in which the fixation means is fixed.

13 Claims, 13 Drawing Sheets

(51) Int. Cl.
*A61B 17/86* (2006.01)
*A61B 17/68* (2006.01)

(56) References Cited

U.S. PATENT DOCUMENTS

| | | | |
|---|---|---|---|
| 5,591,168 A | 1/1997 | Judet et al. | |
| 6,238,417 B1 * | 5/2001 | Cole | 606/213 |
| 6,306,140 B1 * | 10/2001 | Siddiqui | 606/315 |
| 6,468,278 B1 | 10/2002 | Muckter | |
| 6,902,567 B2 | 6/2005 | Del Medico | |
| 7,070,601 B2 * | 7/2006 | Culbert et al. | 606/71 |
| 7,625,395 B2 * | 12/2009 | Muckter | 606/300 |
| 7,780,710 B2 | 8/2010 | Orbay et al. | |
| 8,317,846 B2 * | 11/2012 | Bottlang | 606/312 |
| 8,398,690 B2 * | 3/2013 | Bottlang et al. | 606/308 |
| 8,740,955 B2 * | 6/2014 | Bottlang et al. | 606/310 |
| 2004/0172030 A1 * | 9/2004 | Tipirrneni | 606/72 |
| 2005/0010224 A1 * | 1/2005 | Watkins et al. | 606/65 |
| 2005/0182406 A1 * | 8/2005 | Orbay et al. | 606/69 |
| 2007/0055248 A1 * | 3/2007 | Zlowodzki et al. | 606/69 |
| 2008/0275508 A1 * | 11/2008 | Haidukewych | 606/280 |
| 2009/0131990 A1 * | 5/2009 | Tipirrneni et al. | 606/301 |
| 2009/0254129 A1 * | 10/2009 | Tipirrneni et al. | 606/309 |
| 2014/0107711 A1 | 4/2014 | Norris et al. | |
| 2014/0296855 A1 * | 10/2014 | Haidukewych | 606/66 |

FOREIGN PATENT DOCUMENTS

| | | |
|---|---|---|
| WO | 2004/049963 | 6/2004 |
| WO | 2004/064603 | 8/2004 |
| WO | 2004/069094 | 8/2004 |
| WO | 2006/065512 | 6/2006 |

* cited by examiner

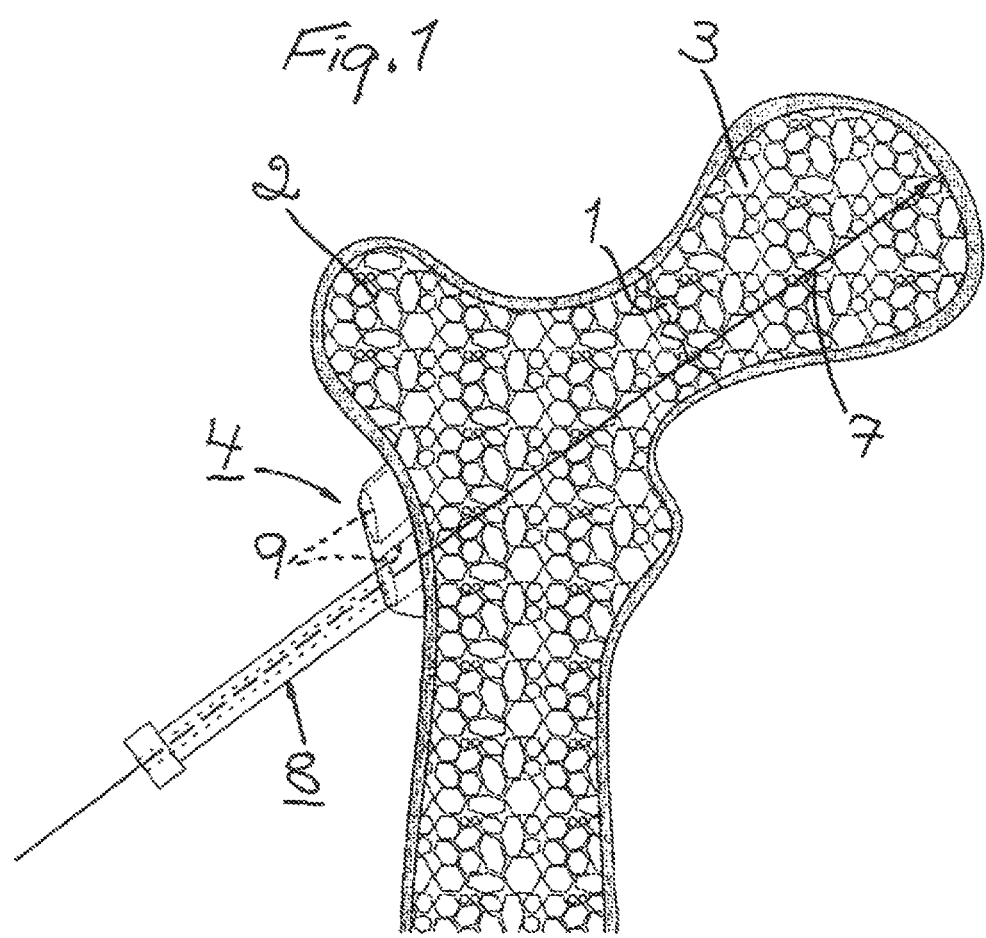

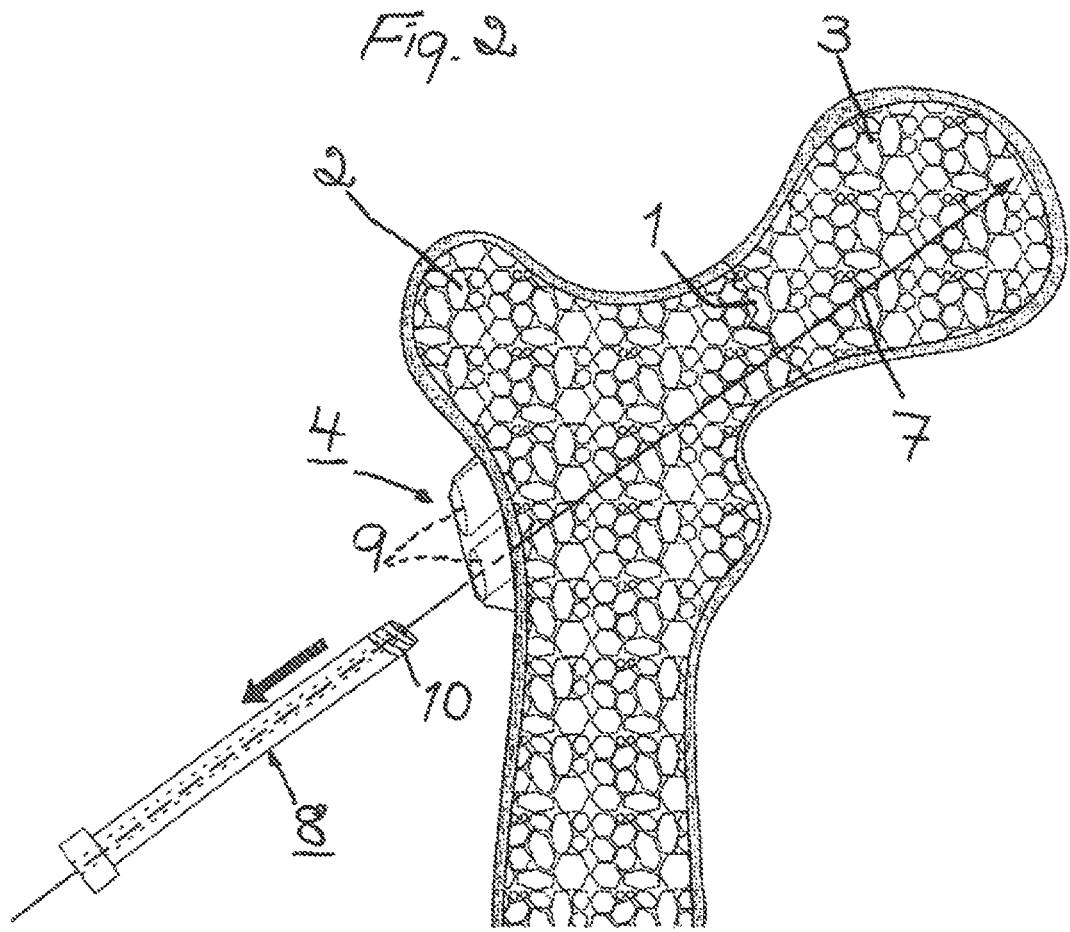

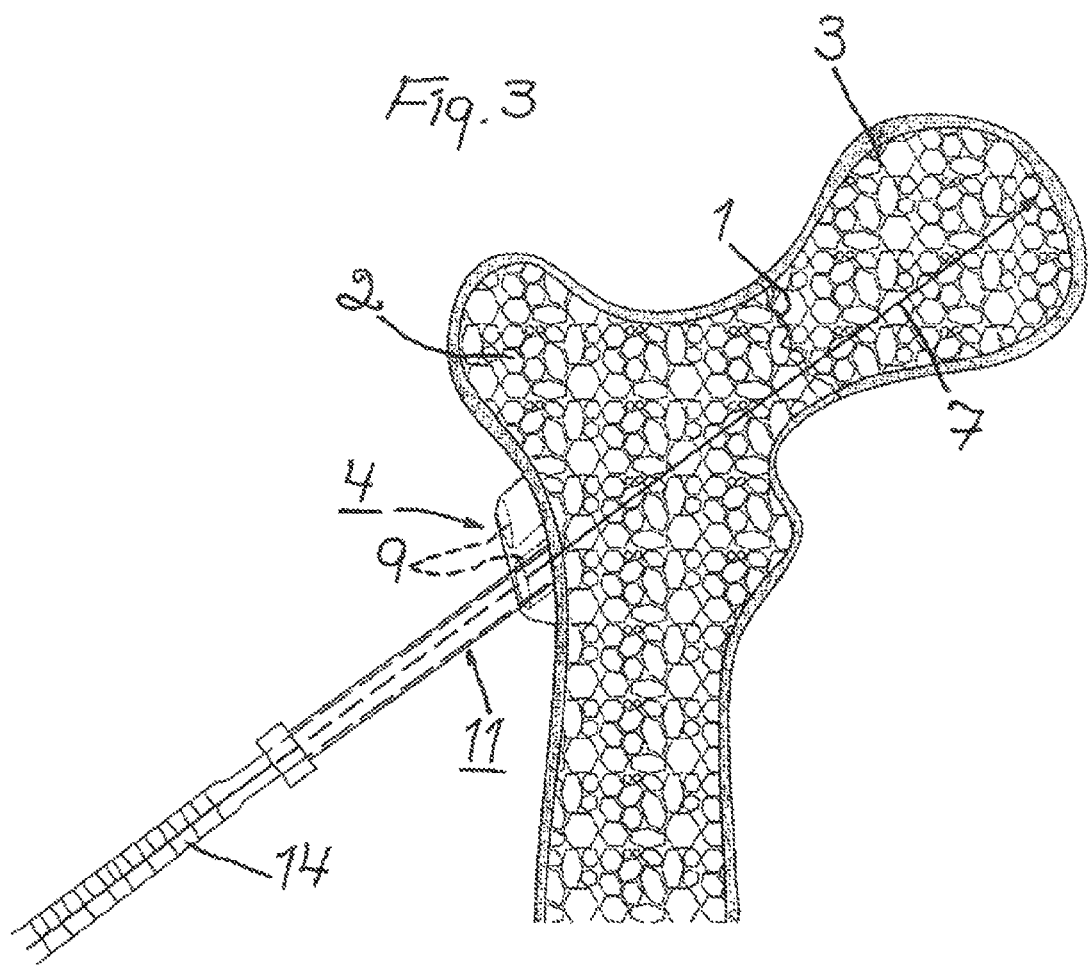

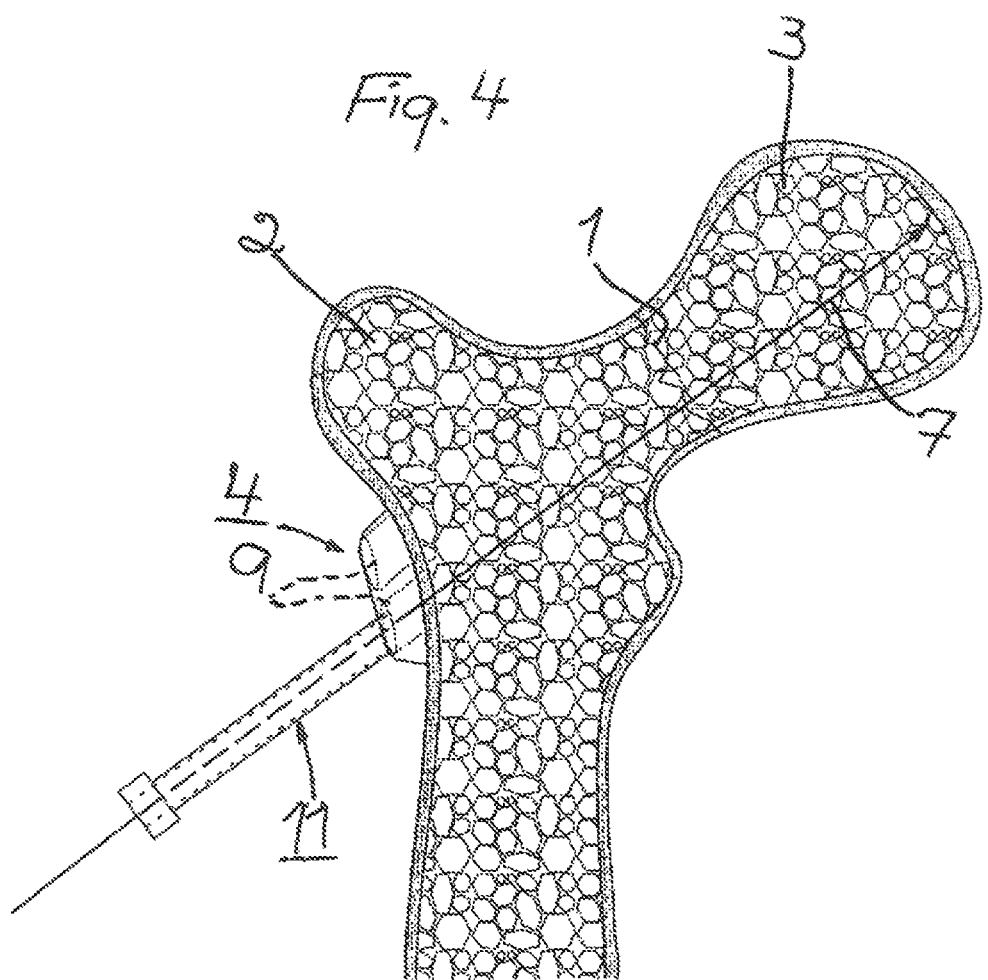

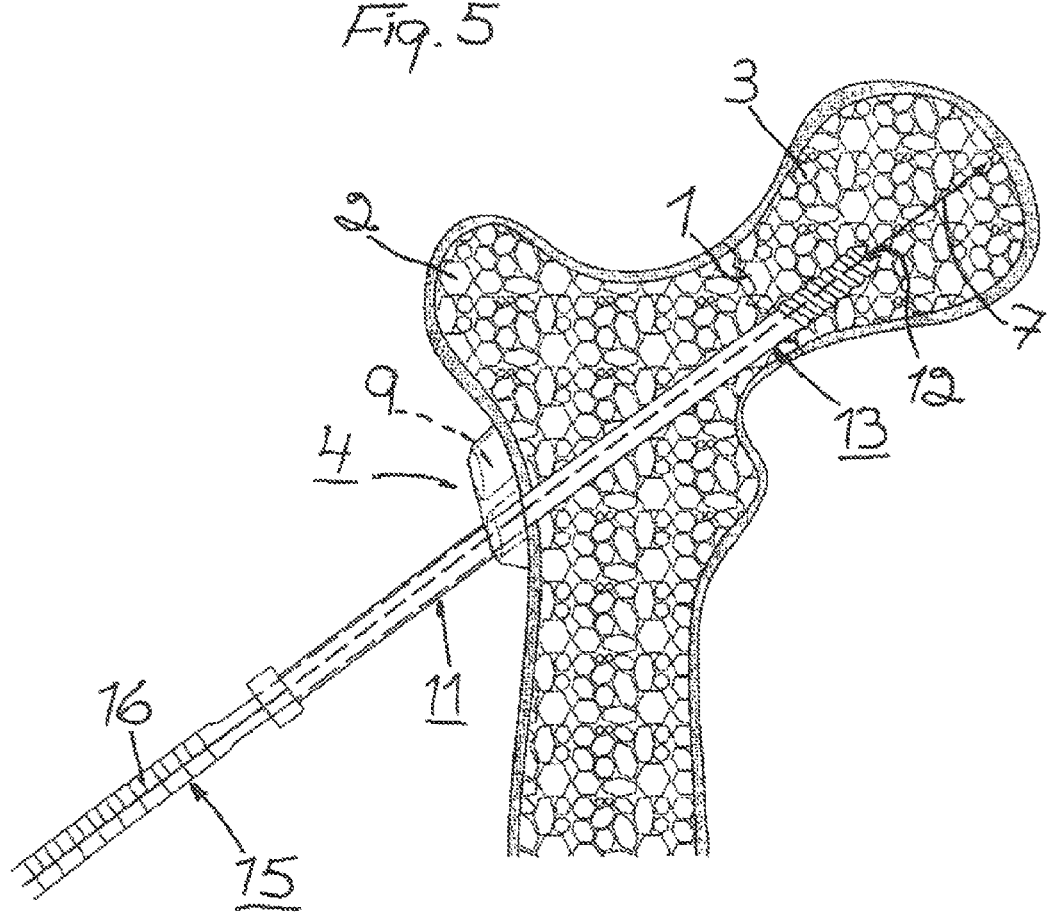

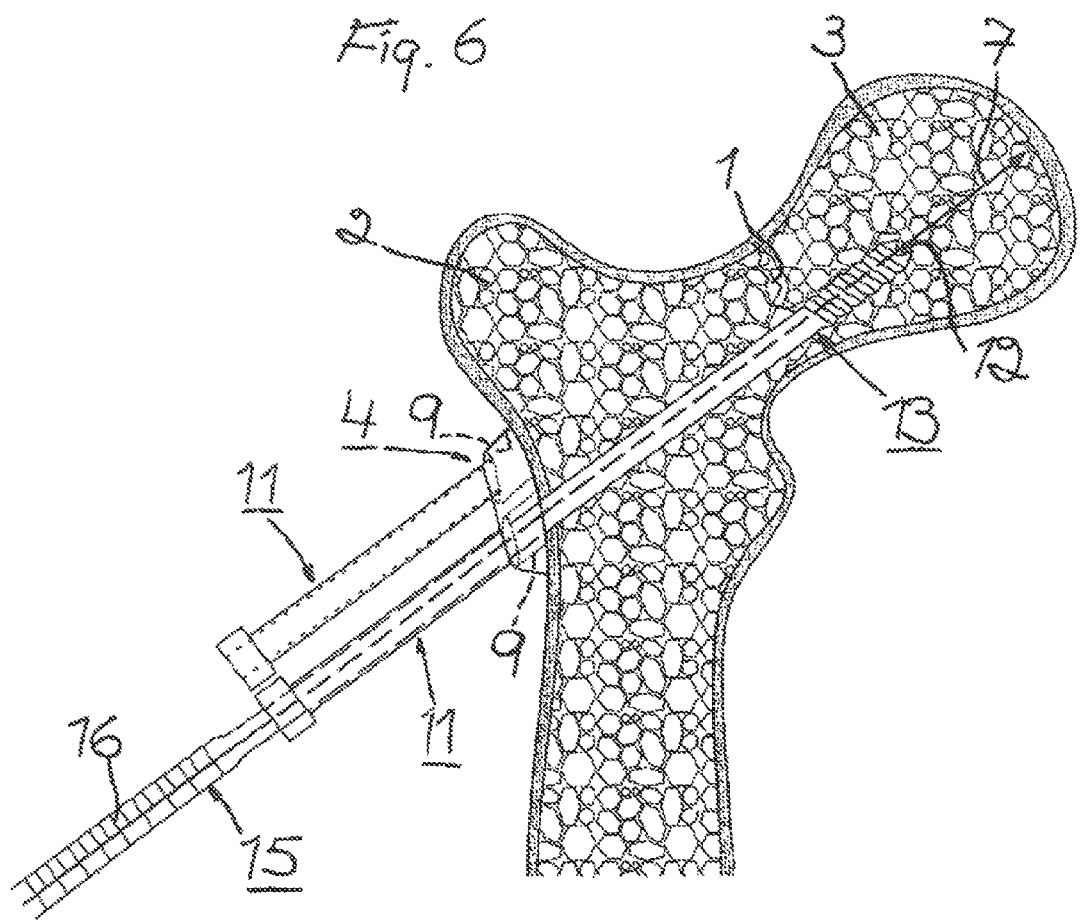

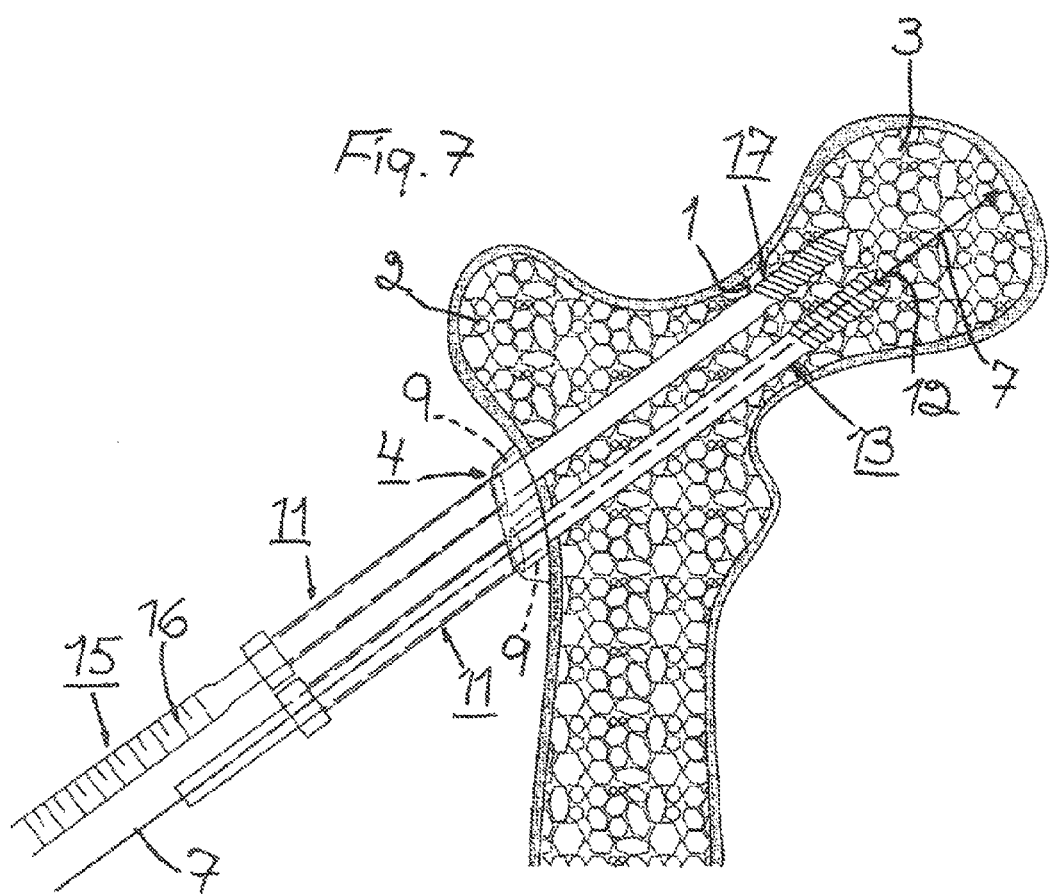

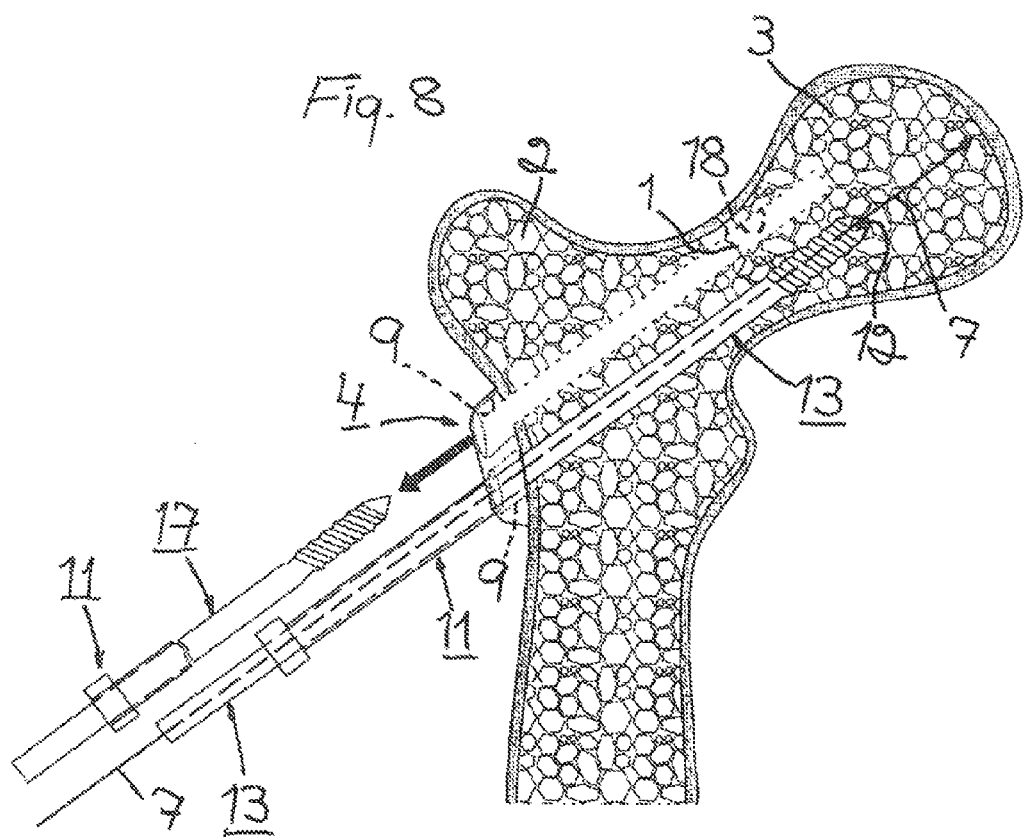

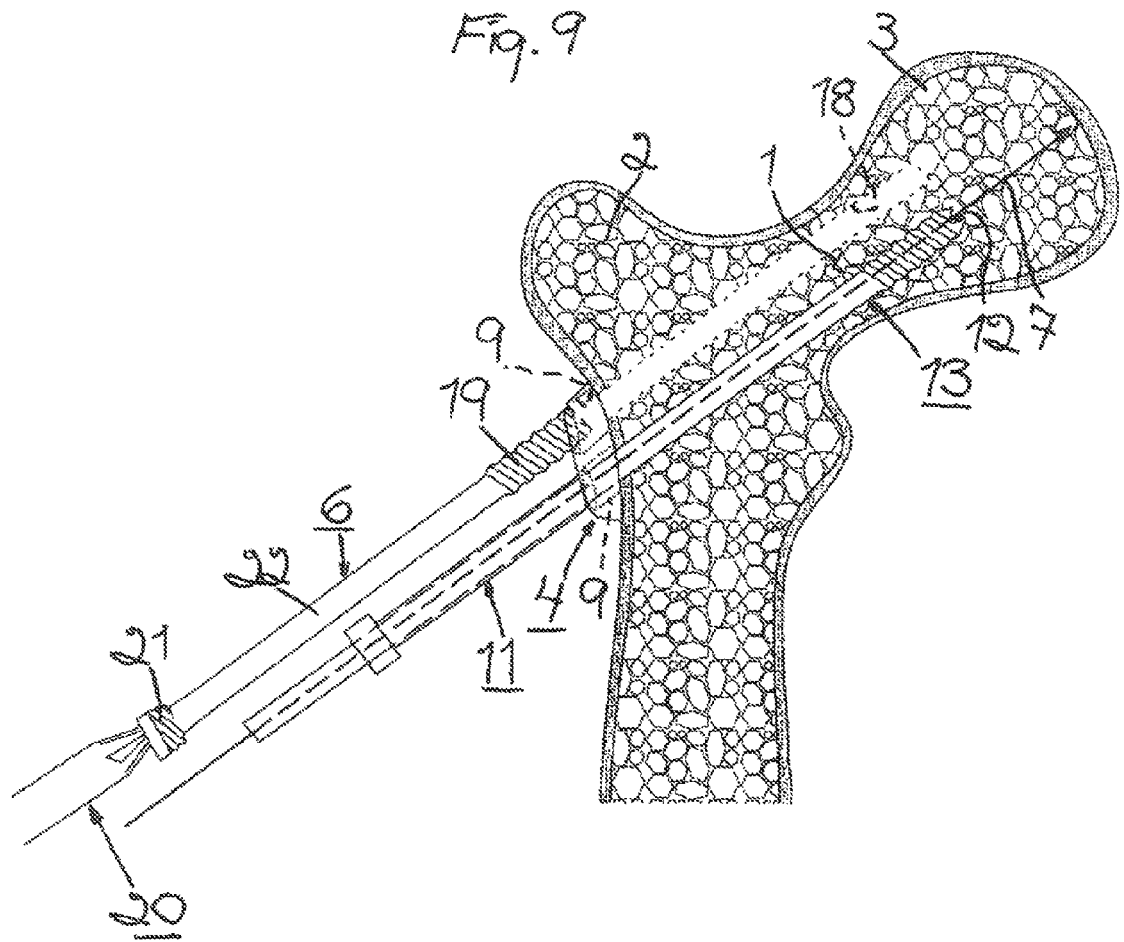

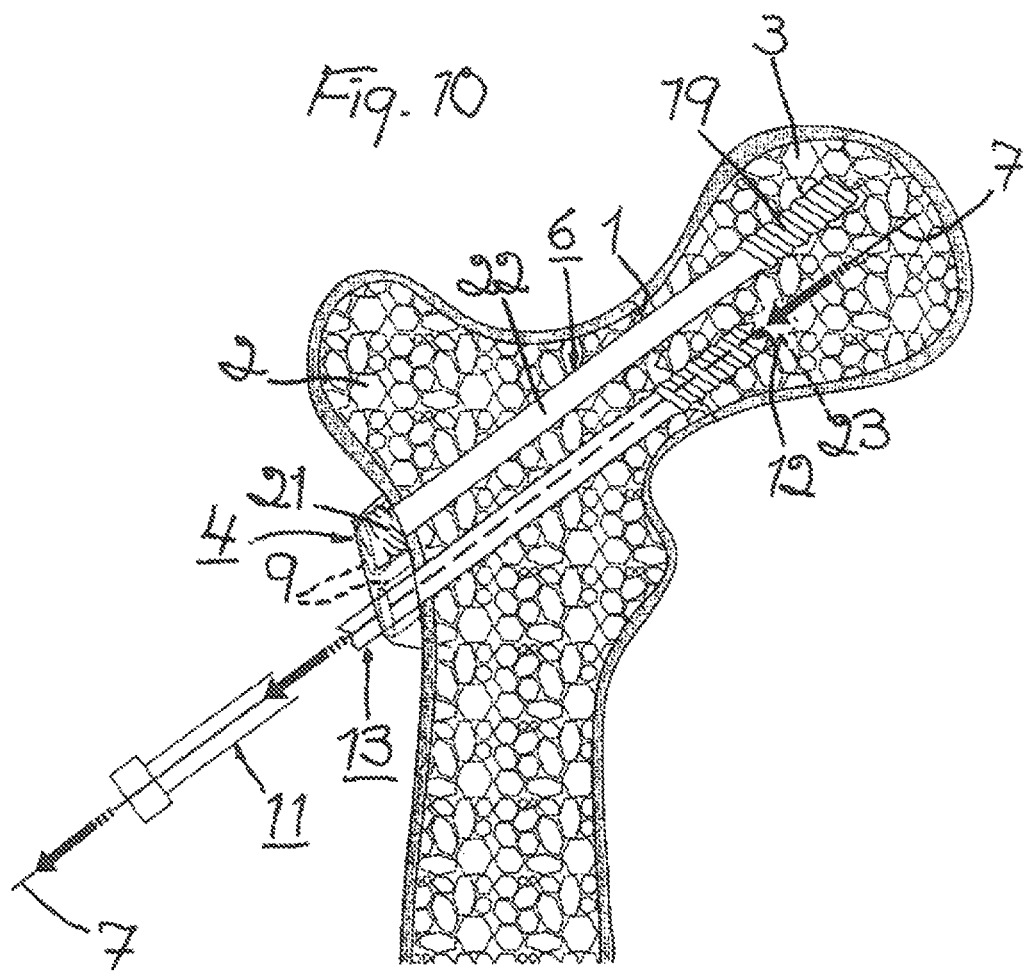

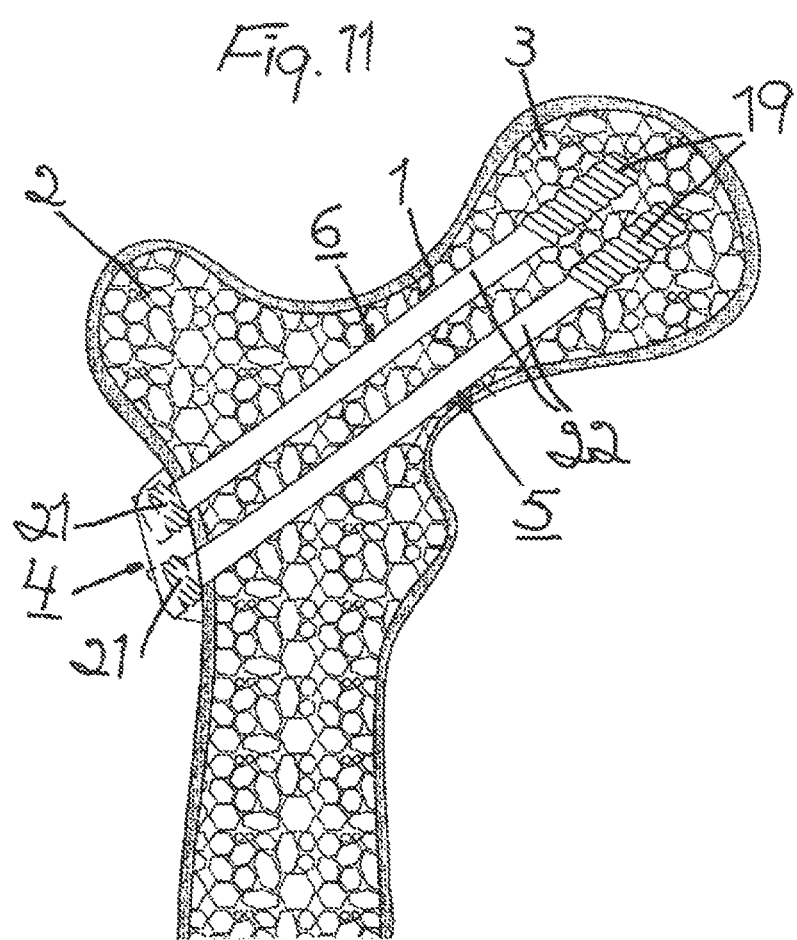

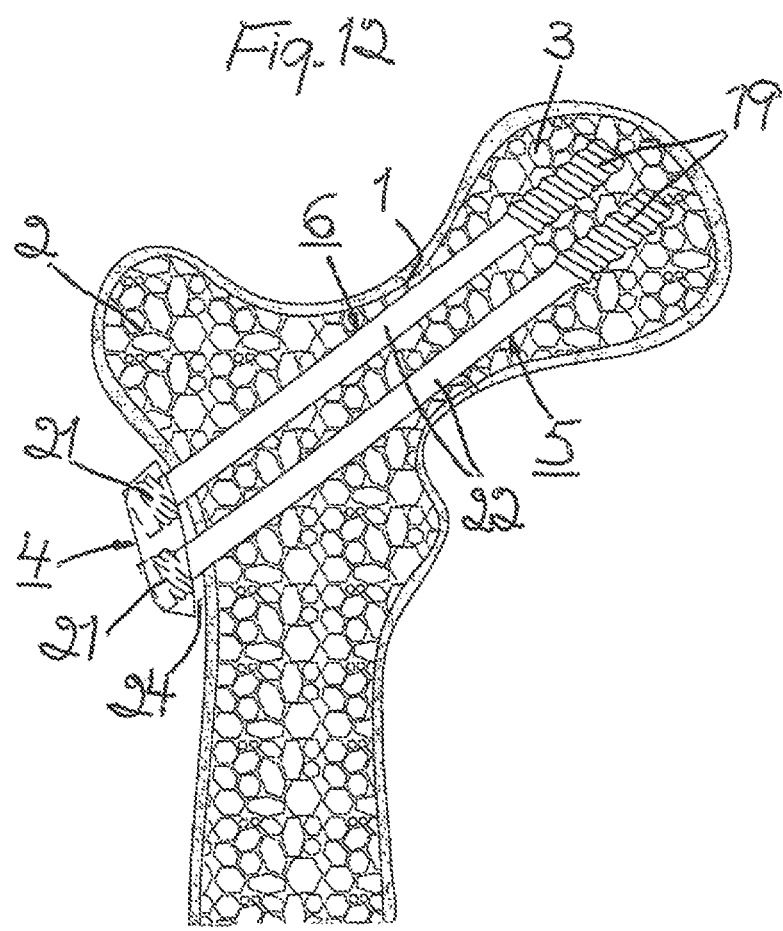

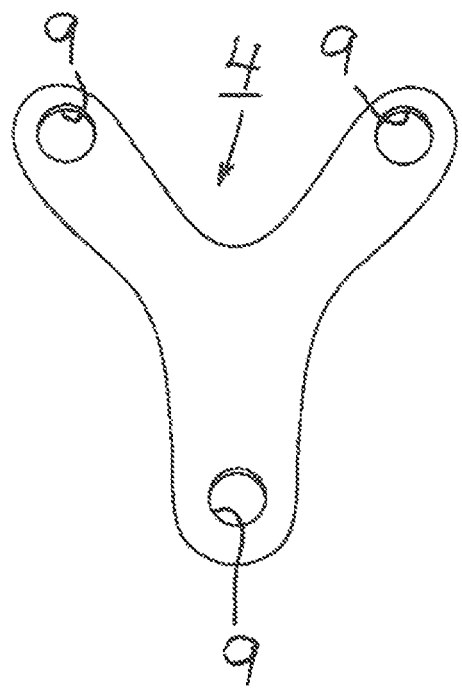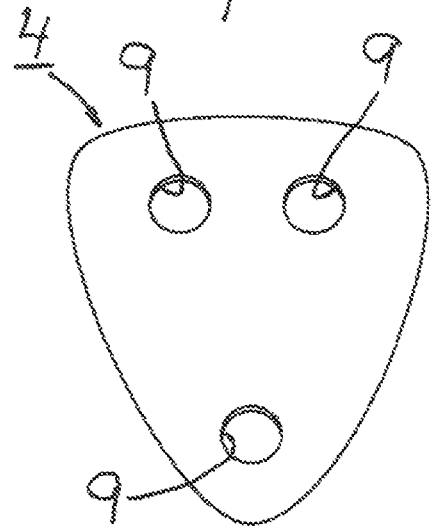

METHOD FOR FIXATION OF BONE FRAGMENTS AT BONE FRACTURES

RELATED APPLICATIONS

This application is a continuation of U.S. Ser. No. 12/670,156, flied May 5, 2010, which corresponds to PCT/SE2008/050848, filed Jul. 8, 2008, which claims the benefit of Swedish Application No. 0701776-7 filed Jul. 24, 2007, the subject matter, of which are incorporated herein by reference in their entirety.

BACKGROUND TO THE INVENTION

The present invention relates to a device for fixation of bone fragments at bone fractures. The device comprises at least two fixation means and a securing plate.

After a bone fracture such as a femur neck fracture, the bone fragments at the fracture need fixing. This is currently done by using suitable fixation means, e.g. bone nails or bone screws.

After the completion of surgery, even as early as when the effects of the anaesthesia have passed and the patient is still confined to bed, but above all when the patient is beginning to be up and walk and stand on the leg, the fixed bone fragments and the fixation means are subject to large forces, particularly to rotational forces downwards and rearwards.

The fixation means alone are often insufficient to counteract these rotational forces and the bone fragments have to be used to help to lock the fracture. If this is not done and the bone fragments are caused to rotate relative to one another by said forces, the result rill be shifting of the angular positions of the fixation means to such an extent that they risk substantially crossing one another, thereby keeping the fracture parted and preventing healing.

The object of the present invention is accordingly to prevent ear counteract this and therefore configure the device in such a way that the fixation means are not allowed to rotate and cross one another.

To this end, with the device according to the invention, each fixation means has a first fixing portion for fixing the fixation means in an inner bone fragment, a second fixing portion for locking the fixation means to the securing plate disposed on the outside of an outer bone fragment and allowing movement if the outer bone fragment relative to it, so that the fixation means are prevented from changing their angular position relative to the securing plate and relative to one another, and a middle portion which is situated between the fixing portions and runs through the outer bone fragment, along which middle portion the outer bone fragment can slide inwards towards the inner bone fragment in which the fixation means is fixed.

The result of the fixation means being thus fixed to the inner bone fragment and to the securing plate while the outer bone fragment can move towards the inner bone fragment and, in so doing, be guided by the fixation means is that the bone fragments are kept fixed but compression of the bone fragments is nevertheless allowed, the device and the bone fragments thus being able to absorb the aforesaid rotational forces and control them so that no re-dislocation occurs. The fixing of the fixation means in the inner bone fragment and the locking of the fixation means to the securing plate also reduce the risk of screws loosening in cases where the fixation means take the form of bone screws.)

BRIEF DESCRIPTION OF THE DRAWINGS

Other objects and advantages of the invention will be apparent to one skilled in the art who examines the attached drawings and the following detailed description of preferred embodiments of and method for fitting the device according to the invention.

FIG. 1 illustrates in side view upper portions of a femur with a femur neck fracture and a device according to the present invention, showing a securing plate and a first guide sleeve usable in conjunction with said plate for guiding a guide wire drilled into gene fragments which are to be fixed on their respective sides of the fracture;

FIG. 2 illustrates in side view the removal of the guide sleeve for the guide wire;

FIG. 3 illustrates in side view a second guide sleeve for guiding a drill, and a gauge rod for determining how long the fixation means should be;

FIG. 4 depicts in side view the second guide sleeve after the removal of the gauge rod;

FIG. 5 illustrates in side view the insertion in the second guide sleeve of a drill, provided with a duct, for drilling a hole for a fixation means in the form of a bone screw and for drilling the hole for said bone screw in the bone fragments;

FIG. 6 depicts in side view the application of a further second guide sleeve for guiding a drill in the securing plate;

FIG. 7 illustrates in side view the further second guide sleeve after the application of a drill with a conical tip therein and the drilling of a second hole for a bone screw in the bone fragments;

FIG. 8 illustrates in side view the removal of the further second guide sleeve and the respective drill;

FIG. 9 depicts in side view the application of a fixation means in the form of a bone screw in the securing plate for further screwing of the bone screw into the second hole in the one fragments;

FIG. 10 illustrates in side view the bone screw when it has been screwed into the bone fragments;

FIG. 11 depicts in side view a second bone screw screwed into the first hole in the bone fragments after the guide wire, drill and guide sleeve have been removed;

FIG. 12 illustrates the securing plate with bone screws screwed firmly into the plate at an alternative five position; and lastly FIGS. 13 and 14 depict front views of two different alternative versions of the securing plate.

DESCRIPTION

The drawings illustrate one of several different methods for fixation of a fracture at the neck of a femur by means of a device according to the present invention. As previously indicated, FIG. 1 depicts upper portions of a femur with a femur neck fracture 1, and an outer bone fragment 2 and an inner bone fragment 3 on their respective sides of the fracture. A securing date 4 which forms part of the device according to the present invention for fixation means in the form of bone screws or bone nails, in the version depicted two substantially parallel bone screws 5, 6 (see FIGS. 9-11) for fixing the bone fragments 4, 3, is disposed on the outside of the outer bone fragment 2. The respective bone screws 5, 6 are preferably integral. The securing plate 4 is so arranged that it allows movement of the outer bone fragment 2 relative to it, i.e. it is not connected to the outer bone fragment nor arranged in some other way whereby it would have moved with the latter upon compression of the bone fragments 2, 3. In the femur, a guide wire 7 with a diameter of preferably about 2.4 mm has been drilled through the outer bone fragment 2 and into the inner bone fragment 3 under radioscopy and with guidance by a guide sleeve 8 with an inside diameter of preferably about 2.5 mm. The guide wire 7 is intended to guide a drill for drilling a hole for the bone screw 5 in the bore fragments 2, 3. According to the invention, the guide sleeve 8 for the guide wire 7 is applied in the securing plate 4, by preferably being screwed firmly in a threaded hole 9 running through the plate, and having for the purpose an externally threaded forward end portion 10 (see FIG. 2 depicting the guide sleeve 8 when it has been unscrewed from the plate 4). This externally threaded forward end portion 10 does of course have an outside diameter corresponding to the diameter of the threaded hole 9 in the securing plate 4, i.e. preferably about 9-10 mm.

After the removal of the guide sleeve 8 for the guide wire 7, a second wide sleeve 11, with an inside diameter of preferably about 6.5 mm and an externally threaded forward portion with the same outside diameter as the first guide sleeve, is applied in, i.e. screwed into, the threaded hole 9 in the securing plate 4 (FIG. 3). This guide sleeve 11 is intended to guide a drill 13, which has running through it a duct 12 for the wire guide 7 (see FIGS. 5-10), for drilling the hole for the bone screw 5 in the bone fragments 2, 3. When the second guide sleeve 11 has been attached to the securing plate 4, a gauge rod 14 is inserted at the rear of this guide sleeve and through the sleeve towards the bone 2, 3. The gauge rod 14 can be used in a conventional manner to indicate how far the drilling should go or how long the bone screw 5 should be for optimum function. In FIG. 4 the gauge rod 14 has been removed.

The hole for the bone screw 5 can now be drilled. Accordingly, as illustrated in FIG. 5, the drill 13 provided with the duct 12 is introduced through the guide sleeve 11 towards the bone fragment 2 and the drilling of the hole for the bone screw 5 is commenced, using a suitable drive device 15. The drill 13 has an outside diameter of preferably about 6.5 mm and fits exactly in the guide sleeve 11. The drill 13 is guided by the guide sleeve 11 to a correct position against the bone fragment 2 and thereafter by the guide wire 7 through the bone fragment 2 and past the fracture 1 into the bone fragment 3. Monitoring that the hole for the bone screw 5 is of a correct length is carried out with advantage at the rear of the guide sleeve 1 where the drill 13 or the drive device 15 bears suitable markings 16. This entails the drill 13 being halted about 2 cm from the tip of the guide wire 7, i.e. about 2 cm before reaching the point to which the bon screw 5 is intended to be screwed in.

After any necessary adjustment of the securing plate 4 sideways, a further second guide sleeve 11 is now applied as per FIG. 6 in a second threaded hole 9 running through the plate. Alternatively, a guide sleeve 8 for a guide wire 7 may be applied first and the same procedure as before, with the same parts as above, may be carried out. With advantage, although not depicted in the drawings, guide sleeves of desired kinds 8, 11 may already from the outset be applied in the respective threaded holes 9 in the securing plate 4 to give the surgeon a better grasp for correct control of the guide wire 7 and the respective drills 13, 17. The guide sleeve 11 in the version depicted is intended to guide a drill 17 without a duct for the guide wire but with a conical tip (see FIG. 7). This solid drill 17 is driven in to a desired position for the bone screw 6 by means of the drive device 15. The correct length is read with advantage at the rear of the guide sleeve 11, where the drill 17 or the drive device 15 bears suitable markings 16 (FIG. 7). The drill 17 and the guide sleeve 11 for it are removed (FIG. 8), leaving a hole 18 for the one screw 6 in the bone fragments 2, 3, which hole is shorter than the distance to which the bone screw is intended to be screwed in.

The bone screw 6 can now, by means of a first fixing portion in the form of a threaded forward end portion 19, be screwed in through the free threaded hole 9 in the securing plate 4 (see FIG. 9) and into the hole 18 in the bone fragments 2, 3 in order to fix these bone fragments. Alternatively, the threaded forward end portion 19 of the bone screw 6 may be somewhat smaller and only be in contact with, i.e. ride on, the threads in the threaded hole 9 in the plate 4. For example, the thread on the threaded forward end portion 19 of the bone screw 6 may be about 8 mm, while the thread in the threaded hole 9 in the securing plate 4 may, as previously indicated, be about 9-10 mm. The bone screw 6 is screwed in by using a suitable tool in the version depicted a suitable type of screwdriver 20. Alternatively it is of course possible to conceive of using for his purpose the same drive device 15 as for the drills 13, 17. The bone screw 6 is screwed in until the second fixing portion in the form of a threaded rear end portion 21 thereof engages in the threaded hole 9 in the securing plate 4 and locks the bone screw to the plate, while at the same time the threaded forward portion 19 of the bone screw is screwed through the outer bone fragment 2 and into the inner bone fragment 3 for engagement therein and locking of the latter bone fragment to the bone screw and the plate, and hence also of the outer bone fragment 2 between the plate and the inner bone fragment. The middle portion 22 of the bone screw 6, which is preferably unthreaded, has with advantage an outside diameter corresponding to that of the drill 17, i.e. about 6.5 m. In FIG. 10 the bone screw 6 is fully screwed in.

In FIG. 11 the drill 13, the guide sleeve 11 for the drill, and the guide wire 7 have been removed. The bone screw 5, preferably similar in form to the bone screw 6, is screwed into the threaded hole 9 in the plate 4 freed by the removal of said items and into the hole 23 created by the drill 13 (FIG. 10) in the bone fragments 2, 3 for fixation of the bone fragments.

The result is a stable connection between the securing plate 4 and the bone screws 5, 6 which prevents the bone screws from changing their angular position relative to the plate and relative to one another in such a way that the bone screws would have crossed one another. There is also optimum fixation of the bone fragments 2, 3 by the bone screws 5, 6.

However, the bone screws 5, 6 are also configured, as a result of their smooth middle portion 22, to allow the bone fragments 2, 3 to be compressed so that the outer bone fragment 2 slides inwards away from the securing plate 4 towards the inner one fragment 3 into which the bone screws are firmly screwed. On such occasions, the securing plate 4 will, through being locked to the bone s move away from its abutment against the outer bone fragment 2 (this is represented schematically in FIG. 12 by the intermediate space 24 between the securing plate and the outer hone fragment), but without affecting the strength of the connection and without any impairment of function.

FIGS. 13 and 14 depict alternative versions of the securing plate 4. The securing plate 4 has in these versions three threaded holes 9 for bone screws.

In all the versions depicted, the threaded holes 9 for the bone screws run substantially parallel with one another so that the bone screws 5, 6 will likewise run substantially parallel with one another. Parallel running of the fixation means facilitates in particular the sliding movement of the outer bone fragment 2 along the fixation means (along the middle portion 22 thereof) for compression of the bone fragments.

The securing plate 4 according to the present invention may be used not only for femur neck (collum femoris) fractures but also for, for example, upper arm (humerus) fractures.

Since during operations for fixation of bone fragments at bone fractures it is important that the fixation means assume exactly predetermined positions relative to the hone fragments and to one another, it is of advantage that the device according to the invention also allows the application of guide sleeves for guidance of drills for drilling holes for the bone screws in the bone fragments, and/or guide sleeves for guidance of guide wires for said drills, in the same holes in the securing plate as are intended for the fixation means. This means that surgical staff need no longer keep count of an unnecessarily large number of different items for performing an operation, operating time becomes shorter and risks and complications for patients are reduced. It will be obvious to one skilled in the art that the device according to the present invention can be modified and altered within the scope of the claims set out below without departing from the idea and objects of the invention. Thus, as indicated above, the securing plate 4 may be used for guide sleeves 8 for guide wires and thereafter for guide sleeves 11 for drills or, for example, immediately for guide sleeves 11 for drills. The securing plate 4 may of course also be used only for guide sleeves 8 for guide wires, followed by drill guidance solely by guide wire, without special guide sleeves for drills. The securing plate 4 may also be used for bone screws of different kinds from the bone screws 5, 6 described above or for other types of fixation means, e.g. bone nails. A bone nail may have a sleeve and, disposed therein, a pin arranged for movement in the sleeve so that at least a forward portion of the pin can be driven outwards through at least one side aperture in the sleeve, in which case this forward portion constitutes a first fixing portion in the form of at least one hook which engages in the inner bone fragment, and the respective bone nail has in addition a second fixing portion of the type described above. As the density in the inner bone fragment is greatest at its centre, it is of advantage if the respective bone nail is applied in such a way that the forward portion of the pin is caused, during the driving, to engage in the central portions of the bone fragment. The respective bone nail may also be so configured as to achieve engagement in the central portions of the inner bone fragment. For example, where there is a threaded second fixing portion, the threads therein may be so disposed and/or configured that said result is achieved. Having the forward portion of the pin in the respective bone nail pointing towards the centre of the inner bone fragment not only means that the bone nails have a better grip in the inner bone fragment but also counteracts the risk of rotation or other movement of the bone nails. Said first and second fixing portions of the fixation means may also be other than threaded portions. The size and choice of material of the constituent items of an operating set may vary as necessary and desired.

The invention claimed is:

1. A method for fixation of inner and outer bone fragments at bone fractures against rotational forces, comprising:
   engaging an outer surface of the outer bone fragment with a securing plate;
   inserting at least two fixation means through the securing plate, through the outer bone fragment, across the fracture, and into the inner bone fragment, each fixation means including a first fixing portion, a second fixing portion, and a middle portion situated between the first and second fixing portions and extending through the outer bone fragment;
   fixing the first fixing portions of the at least two fixation means to the inner bone fragment;
   fixing the second fixing portions of the at least two fixation means to the securing plate to prevent relative movement in proximal and distal directions between the second fixing portions and the securing plate; and
   permitting sliding movement of the outer bone fragment along the middle portions relative to the securing plate towards the inner bone fragment and away from the securing plate during compression of the outer bone fragment and the inner bone fragment when the second fixing portions are fixed to the securing plate.

2. A method according to claim 1 wherein the step of inserting the at least two fixation means through the securing plate is preceded by threading guide sleeves to the securing plate for guidance of drills intended to drill holes for the fixation means in the bone fragments, and/or of guide sleeves for guidance of guide wires intended to guide the drills during the drilling.

3. A method according to claim 1 wherein each of the at least two fixation means includes a bone screw, the fixing of first fixing portions to the inner bone fragment including threading forward ends of the bone screws into the inner bone fragment.

4. A method according to claim 1 wherein each of the at least two fixation means includes a bone nail having a sleeve and a pin movable within the sleeve, the fixing of first fixing portions to the inner bone fragment including driving at least forward portions of the pins outwards through at least one side aperture in the sleeves so that the pins form hooks in the inner bone fragment.

5. A method according to claim 4 including driving the forward portions of the pins into central portions of the inner bone fragment.

6. A method according to claim 1 wherein fixing second fixing portions of the at least two fixation means to the securing plate includes threadably engaging the second fixing portions to the securing plate.

7. A method according to claim 1 further including extending the at least two fixation means parallel to each other when the first fixing portions are fixed to the inner bone fragment and the second fixing portions are fixed to the securing plate.

8. A method according to claim 7 wherein all fixation means extending through the securing plate and into the outer bone fragment extend parallel to each other.

9. A method according to claim 1 including disposing the securing plate adjacent a lateral side of a femur having a neck fracture forming the inner bone fragment and the outer bone fragment that includes a head of the femur.

10. A method according to claim 1 including maintaining the angular orientation and the axial position of the at least two fixation means with respect to the securing plate.

11. A method according to claim 1 wherein the middle portions are formed as one piece with the second fixing portions.

12. A method according to claim 1 wherein the second fixing portions are threaded into the securing plate to prevent relative axial movement between the fixation means and the securing plate.

13. A method for fixation of inner and outer bone fragments at bone fractures against rotational forces, comprising:
   providing at least two fixation means each having a first fixing portion, a second fixing portion, and a middle portion extending between the first and second fixing portions;
   engaging an outer surface of the outer bone fragment with a securing plate;
   inserting the at least two fixation means through the securing plate, through the outer bone fragment, across the fracture, and into the inner bone fragment such that the middle portions of the at least two fixation means extend through the outer bone fragment;
   fixing the first fixing portions of the at least two fixation means to the inner bone fragment;
   threadably engaging the second fixing portions of the at least two fixation means with the securing plate to prevent relative axial movement between the fixation means and the securing plate; and permitting sliding movement of the outer bone fragment along the middle portions relative to the securing plate towards the inner bone fragment and away from the securing plate during compression of the outer bone fragment and the inner bone fragment when the second fixing portions are fixed to the securing plate.

* * * * *